United States Patent
Lukica et al.

(10) Patent No.: US 6,218,666 B1
(45) Date of Patent: Apr. 17, 2001

(54) METHOD OF DETERMINING THE CONCENTRATION OF A GAS IN A GAS MIXTURE AND ANALYZER FOR IMPLEMENTING SUCH A METHOD

(75) Inventors: Ivan Gavrilovic Lukica; Jemeljan Mihailovic Gamartz; Vladimir Arkadevic Krilov; Svetlana Igorevna Francuzova, all of Saint Petersbourg (RU)

(73) Assignee: Oldham France S.A., Arras Cedex (FR)

( * ) Notice: Subject to any disclaimer, the term of this patent is extended or adjusted under 35 U.S.C. 154(b) by 0 days.

(21) Appl. No.: 09/205,193

(22) Filed: Dec. 4, 1998

(30) Foreign Application Priority Data

Dec. 5, 1997 (FR) .................................................. 97 15422

(51) Int. Cl.[7] .................................................. G01N 21/61
(52) U.S. Cl. ........................................ 250/343; 250/338.1
(58) Field of Search ................................. 250/343, 338.1

(56) References Cited

U.S. PATENT DOCUMENTS

| 3,958,122 | 5/1976 | Jowett et al. . | |
|---|---|---|---|
| 4,579,456 | * 4/1986 | Gramont | 250/338.1 |
| 5,281,817 | * 1/1994 | Yelderman et al. | 250/343 |
| 5,572,031 | 11/1996 | Cooper et al. . | |
| 5,585,635 | * 12/1996 | Graham | 250/343 |

FOREIGN PATENT DOCUMENTS

| 31 16344 A1 | 11/1982 | (DE) . |
| 0 084 726 A1 | 8/1983 | (EP) . |
| 0 318 752 | 6/1989 | (EP) . |
| 58-135940 | 8/1983 | (JP) . |
| 61-097552 | 5/1986 | (JP) . |
| 6-222003 | 8/1994 | (JP) . |
| 6-281477 | 10/1994 | (JP) . |

* cited by examiner

*Primary Examiner*—Constantine Hannaher
*Assistant Examiner*—Otilia Gabor
(74) *Attorney, Agent, or Firm*—Young & Thompson

(57) ABSTRACT

In this method of determining the concentration of a gas to be analyzed in a gas mixture, the value of a characteristic of the gas mixture having predetermined laws of variation as a function of temperature and of the gas concentration is calculated from at least one measured value of the intensity of at least one radiation transmitted through the mixture at ambient temperature, the value of the said characteristic at a reference temperature is determined from the law of variation of the characteristic as a function of temperature and the value of the gas concentration is determined from the law of variation of the said characteristic as a function of the concentration.

8 Claims, 2 Drawing Sheets

METHOD OF DETERMINING THE CONCENTRATION OF A GAS IN A GAS MIXTURE AND ANALYZER FOR IMPLEMENTING SUCH A METHOD

FIELD OF THE INVENTION

The present invention relates to a method of determining the concentration of a gas to be analysed contained in a gas mixture by optical absorption spectroscopy, and an analyser for implementing such a method.

BACKGROUND OF THE INVENTION

In this type of method, the concentration of the gas is determined from its optical absorption characteristics by measuring the intensity of radiation in various wavelength bands transmitted through the gas mixture.

This technique is very sensitive to temperature and gives variable results when the ambient temperature changes, on the one hand because of the resulting modification of the characteristics of the components making up the analyser, in particular the semiconductor-based optical components, and on the other hand because of the variation in the absorption spectrum of the gas to be analysed as a function of temperature, this variation being due in particular to a variation in its density.

In order to compensate for the measurement errors caused by the variation in the sensitivity of the optical components as a function of temperature, it is known to introduce, into the analyser, a thermistor, the temperature coefficient of which is chosen so as to be equal to that of the photoreceiver optical component, associated with an adjusting resistor in order to set the information provided by the analyser to zero in the absence of the gas to be analysed. Thus, the influence of temperature on the photoreceiver is neutralized.

Moreover, in order to neutralize the influence of temperature on the absorption spectrum, a diode is used whose temperature dependence is similar to that of the absorption spectrum of the gas to be analysed. This diode controls a calibrating voltage supplied to the radiation source so as to compensate for the variation in gas density.

This technique requires a prior step of calibrating the analyser, during which an optical analysis cell is filled with a gas at a known concentration N and the calibrating signal is adjusted so that the information provided corresponds to this concentration value.

This technique has a number of drawbacks, especially because the calibration operation must be carried out again when the ambient temperature changes.

Furthermore, these operations are not always able to be accomplished in that it is not possible to determine, using an uncalibrated device, the absence or presence of the gas to be analysed in the environment.

Moreover, the compensating elements, such as the thermistors or diodes, only allow an approximate compensation to be made for the temperature dependence of the sensitivity of the photoreceiver and of the absorption spectrum of the gas to be analysed.

Finally, this type of method does not make it possible to compensate for the variation in the characteristics of the components other than the photoreceiver.

The object of the invention is to overcome the aforementioned drawbacks.

SUMMARY OF THE INVENTION

The subject of the invention is therefore a method of determining the concentration of a gas to be analysed in a gas mixture, by measuring at least one value of the intensity of at least one radiation transmitted through the mixture, characterized in that it comprises the steps consisting in:

calculating, from at least one measured value of the intensity of at least one radiation transmitted at ambient temperature, the value of a characteristic of the gas mixture having predetermined laws of variation as a function of temperature and as a function of the concentration of gas to be analysed;

determining the value of the said characteristic at a predefined reference temperature different from the ambient temperature from the law of variation of the characteristic as a function of temperature; and determining the value of the concentration of the gas from the law of variation of the said characteristic as a function of the concentration.

The method according to the invention may furthermore comprise one or more of the following characteristics:

the law of variation of the said characteristic as a function of the concentration is determined during a prior calibration step by determining a set of values of the characteristic for various gas concentrations and at the reference temperature;

the characteristic consists of the transmission coefficient $T(N,t)$ of the gas mixture, defined by the equation:

$$T(N, t) = \frac{U(N, t)}{U(0, t)} \quad (1)$$

in which:

$T(N,t)$ denotes the transmission coefficient at the temperature t of the gas mixture containing a concentration N of the gas to be analysed; and $U(N,t)$ and $U(0,t)$ denote the intensity of an electrical signal formed from the output of the means for detecting the radiation transmitted through the gas mixture, at the temperature t, the mixture containing a concentration N and a zero concentration of the gas to be analysed, respectively, and the intensity of the electrical signal $U(0,t)$ formed from a mixture containing a zero concentration of gas to be analysed being obtained during the prior calibration step;

during the prior calibration step, the intensity of the electrical signal is measured at the reference temperature for various values of the concentration of the gas to be analysed and in the absence of the gas to be analysed in the gas mixture and, for each concentration value, the transmission coefficient is calculated;

the value of the transmission coefficients at the reference temperature is determined during the analysis of the gas mixture from the following equation:

$$T(N, t_{ref}) = T(N, t_a)^{\frac{\ln T(N_0, t_{ref})}{\ln T(N_0, t_a)}} \quad (2)$$

or from the equation:

$$T(N, t_{ref}) = 1 - (1 - T(N, t_a)) \frac{1 - T(N_0, t_{ref})}{1 - T(N_0, t_a)} \quad (3)$$

in which:

$T(N,t_{ref})$ and $T(N,t_a)$ denote the transmission coefficient of the gas mixture for a concentration N of the gas to be analysed at the reference temperature and at the ambient temperature, respectively; and $T(N_0, t_{ref})$ and $T(N_0, t_a)$ denote the value of the transmission coefficient of the gas mixture for a pre-determined concentration $N_0$ of the gas to be analysed at the reference temperature and at the ambient temperature, respectively;

during the prior calibration step, the intensity of the electrical signal is measured for the said gas concentration $N_0$ and for various temperature values encompassing the reference temperature and the ambient temperature, and, for each temperature value, the transmission coefficient is calculated.

The subject of the invention is also an analyser for determining the concentration of a gas in a gas mixture contained in an optical analysis cell, comprising means for emitting a radiation through the optical cell and means for detecting the radiation transmitted, both these means being connected to means for calculating the concentration of the gas, characterized in that the means for calculating the concentration of the gas comprise means for calculating the transmission coefficient of the gas mixture, at ambient temperature, means for calculating the corresponding value of the transmission coefficient at a reference temperature different from the ambient temperature and means for calculating the concentration of the gas by comparing the calculated value of the transmission coefficient at the reference temperature with a set of predetermined values stored in a memory, each value corresponding to a concentration value of the gas.

BRIEF DESCRIPTION OF THE INVENTION

Further features and advantages will emerge from the following description, given solely by way of example and with reference t the appended drawings in which.

DETAILED DESCRIPTION OF THE INVENTION

Figure 1:
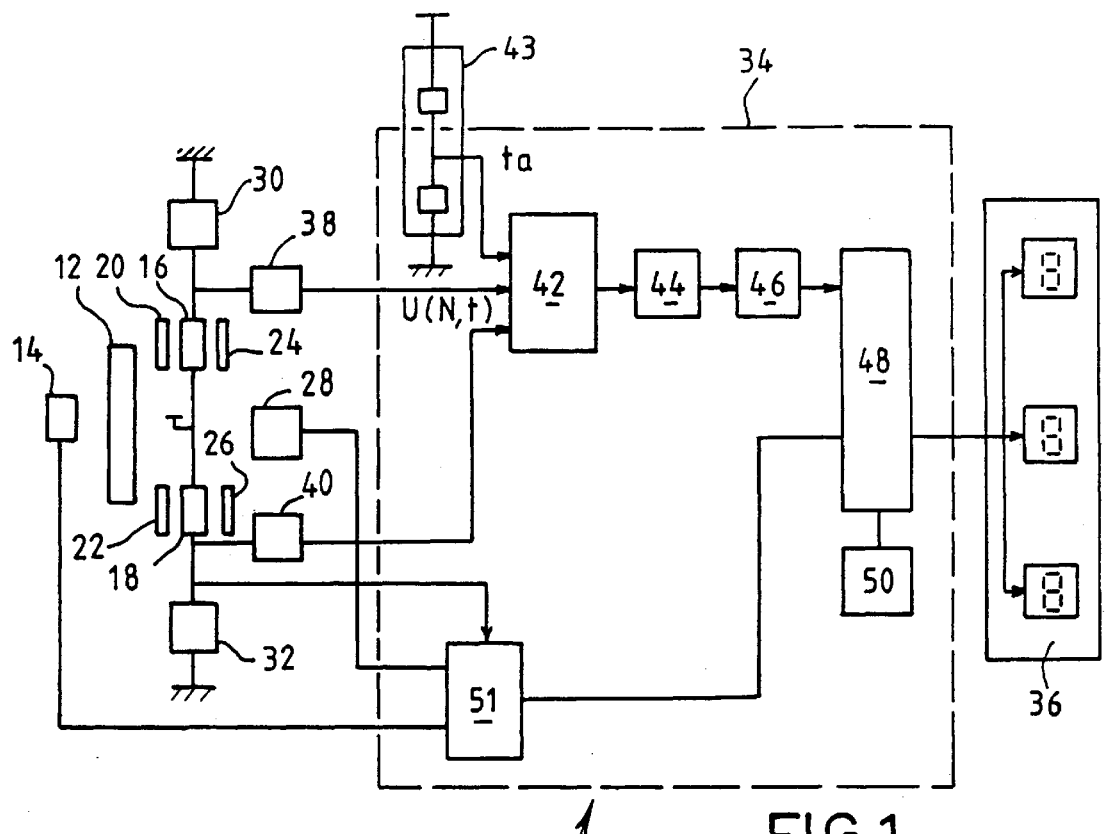
FIG. 1 is a block diagram of an analyser according to the invention, for analysing a gas mixture, allowing the determination of the concentration of a gas to be analysed contained in this mixture.

Shown in FIG. 1 is a gas analyser, denoted by the general numerical reference 10, intended to determine the concentration of a gas contained in a gas mixture contained in a conventional type of optical analysis cell 12.

This analyser comprises radiation-emitting means which face the cell 12 and consist of a light-emitting diode 14 emitting, for example, radiation in the infrared range, and means for detecting the radiation transmitted through the cell 12, these means consisting of photo-detectors 16 and 18 lying on the optical path of the radiation delivered by the light-emitting diode 14, one of them, 16, consisting of a measurement photodetector and the other, 18, consisting of a reference photo-detector.

The photodetectors 16, 18 measure at least one value of the intensity of at least one radiation transmitted through the gas mixture.

Each photodetector is associated with a first filter, 20 and 22 respectively, interposed between the cell 12 and the corresponding photodetector 16, 18 and with a second filter, 24 and 26 respectively, interposed between the corresponding photodetector and a calibration light source consisting of a light-emitting diode 28 similar to the diode 14 and making it possible, as is conventional, to calibrate the gain of the system for measuring the radiation transmitted through the optical analysis cell 12.

The filters associated with the measurement photodetector 16 filter the radiation so as to remove those components of the absorption spectrum which lie outside those of the gas to be analysed which is present in the gas mixture, whereas the filters associated with the reference photodetector 18 are designed to filter the radiation so as to remove the spectral components corresponding to those of the gas to be analysed.

This FIG. 1 also shows that the output of each photodetector 16 and 18 is connected, on the one hand, to earth via a load resistor 30 and 32, respectively, and to the input of a signal-processing unit 34, the output of which is connected to a display device 36 and, on the other hand, to a DC power supply.

More particularly, this FIG. 1 shows that the output of each photodetector 16 and 18 is connected via a dividing amplifier, 38 and 40 respectively, to a multiplexer 42 of the unit 34, which multiplexer 42 also receives, as input, a measurement signal $t_a$ of the ambient temperature delivered by a suitable sensor consisting, for example, of a thermistor 43.

The multiplexer 42 is connected, on the output side, to an amplifier 44 and, via an analog-to-digital converter 46, to a microprocessor 48 associated with storage means 50 in which are stored one or more algorithms for calculating the concentration of the gas to be analysed contained in the gas mixture contained in the optical analysis cell 12.

Finally, this figure shows that the microprocessor 48 is also connected to the display device 36, for the purpose of presenting an operator with data relating to the value of the calculated concentrations, and to a circuit 51 for controlling the light sources 14 and 28.

The method of determining the concentration of the gas contained in the gas mixture used in the device 10 which has just been described is carried out in the following manner.

In the rest of the description, it will be assumed that the gas mixture contained in the cell 12 consists of a nitrogen/methane mixture, the methane concentration of which is to be determined. Of course, the invention also applies to the analysis of other gases.

First of all, a prior calibration step is carried out during which the electrical signal $U(0,t)$, formed from the output of the photodetectors 16 and 18 by calculating the ratio between the outputs of these photodetectors for a gas mixture having a zero concentration of the gas to be analysed, and therefore consisting of nitrogen, for several temperature values corresponding to the temperature range over which the device is used, is stored in the memory 50. A law of variation of the electrical signal $U(0,t)$ as a function of temperature is thus formed.

During this calibration step, the electrical signal $U(N_0,t)$ corresponding to the signal delivered by the photodetector 38 for a gas mixture having a pre-determined methane concentration $N_0$, for several temperature values corresponding to the temperature range over which the device 10 is used, is recorded. Thus, a law of variation of the electrical signal $U(N_0,t)$ as a function of temperature is formed.

Moreover, during this calibration step, the value of the electrical signal $U(N,t_{ref})$ for various methane concentration values corresponding to the concentration range able to be measured by the apparatus, and for a predetermined reference temperature value $t_{ref}$ different from the ambient temperature, is formed from the output of the photodetectors 16 and 18 and is stored in the memory 50. Thus, a law of variation in the electrical signal $U(N,t_{ref})$ as a function of the concentration of the gas to be analysed, that is to say as a function of the methane concentration, is formed.

From the measured and stored values of the electrical signal $U(N_0,t)$ obtained for a methane concentration $N_0$ and for various temperature values t, and from the electrical signal $U(0,t)$ formed for a zero methane concentration and for various temperature values t, a characteristic of the gas mixture, the law of variation of which as a function of temperature is known, is calculated for each of the temperature values.

This characteristic consists of the transmission coefficient $T(N,t)$, also known as the standardized transmittance or transmission factor, of the gas mixture, this characteristic being defined by the following equation:

$$T(N, t) = \frac{U(N, t)}{U(0, t)} \qquad (1)$$

Likewise, during this calibration step, the microprocessor 48 calculates, from the values of the electrical signal $U(N, t_{ref})$ which are obtained for various methane concentration values at the reference temperature $t_{ref}$ and from the value of the electrical signal $U(0,t_{ref})$ obtained for a zero methane concentration at the reference temperature $t_{ref}$, the value of the transmission coefficient $T(N,t_{ref})$ for each of these concentration values N by means of Equation (1).

Figure 2:
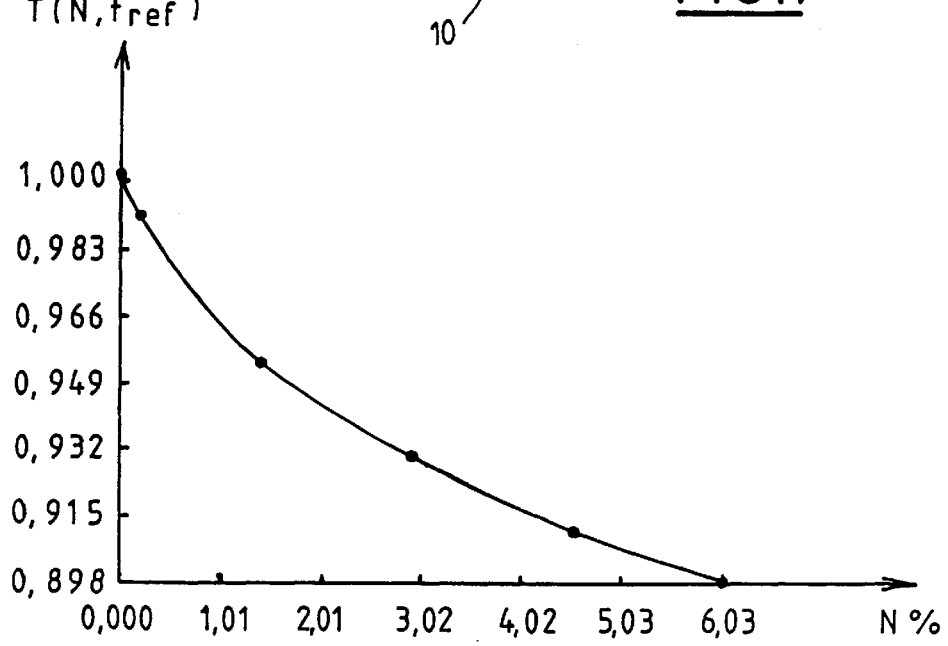
FIG. 2 is a curve showing the variation in the transmission coefficient as a function of the concentration of the gas, at the reference temperature.
Figure 3:
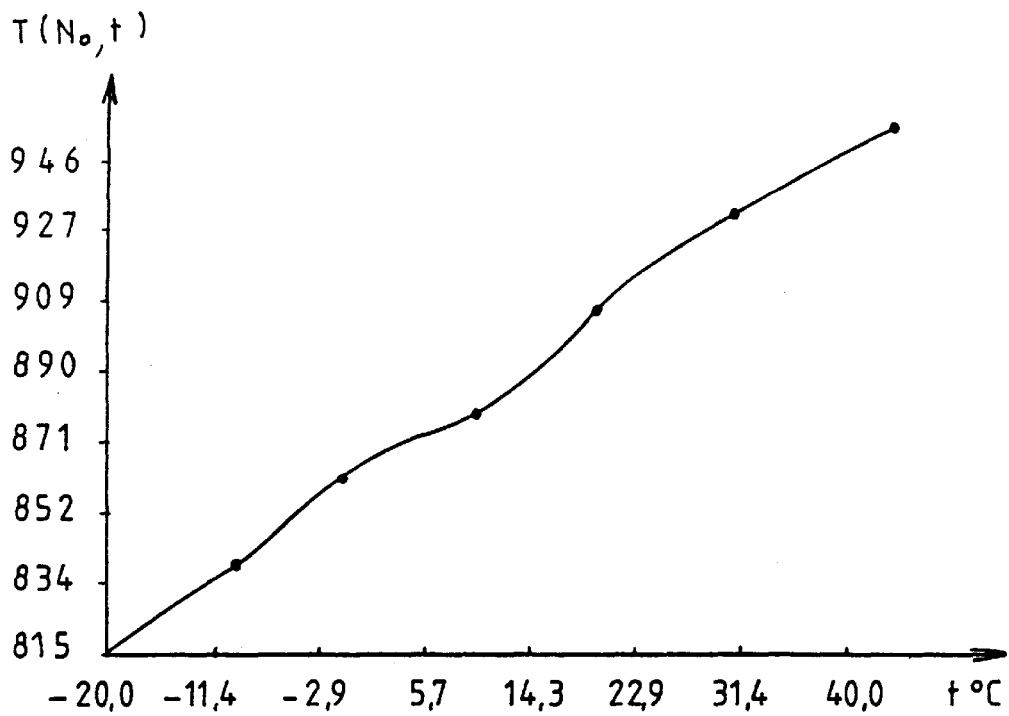
FIG. 3 is a curve showing the variation in the transmission coefficient as a function of temperature, at a fixed concentration of the gas to be analysed.

Thus, the laws of variation of the transmission coefficient, on the one hand, as a function of the concentration, at a fixed reference temperature $t_{ref}$, and, on the other hand, as a function of temperature, for a fixed predetermined concentration $N_0$, respectively $T(N,t_{ref})$ and $T(N_0,t)$ shown in FIGS. 2 and 3 are formed.

After this prior calibration step, when the optical analysis cell 12 is filled with a gas mixture consisting of nitrogen and methane and containing an unknown methane concentration N, at an ambient temperature $t_a$ measured by the thermistor 43, the value of the electrical signal $U(N,t_a)$ is calculated from the output of the photodetectors 16 and 18 which is delivered, via the multiplexer 42, the amplifier 44 and the analog-to-digital converter 46, to the microprocessor 48.

The latter extracts from the memory 50 on the basis of the value of the ambient temperature $t_a$, the value of the electrical signal $U(0,t_a)$ corresponding to the electrical signal calculated from the output of the photodetectors 16 and 18 for a zero methane concentration at the ambient temperature $t_a$.

It then calculates the corresponding value of the transmission coefficient $T(N,t_a)$ using the abovementioned formula (1).

The microprocessor 48 then calculates, using a suitable computing algorithm stored in the memory 50, the corresponding value of the transmission coefficient $T(N,t_{ref})$ at the reference temperature at which the calibration was carried out, using the following equation:

$$T(N, t_{ref}) = T(N, t_a)^{\frac{\ln T(N_0, t_{ref})}{\ln T(N_0, t_a)}} \qquad (2)$$

or from the following equation obtained by a limited amount of development:

$$T(N, t_{ref}) = 1 - (1 - T(N, t_a)) \frac{1 - T(N_0, t_{ref})}{1 - T(N_0, t_a)} \qquad (3)$$

The value thus calculated of the transmission coefficient $T(N,t_{ref})$ at the reference temperature allows the value of the concentration of the gas to be analysed contained in the gas mixture to be obtained directly from the law of variation of the transmission coefficient $T(N,t_{ref})$ as a function of the concentration of the gas to be analysed, at the reference temperature $t_{ref}$, shown in FIG. 2.

The method of analysis which has just been described allows the actual value of the concentration of a gas contained in a gas mixture to be accurately determined whatever the ambient temperature.

Figure 4:
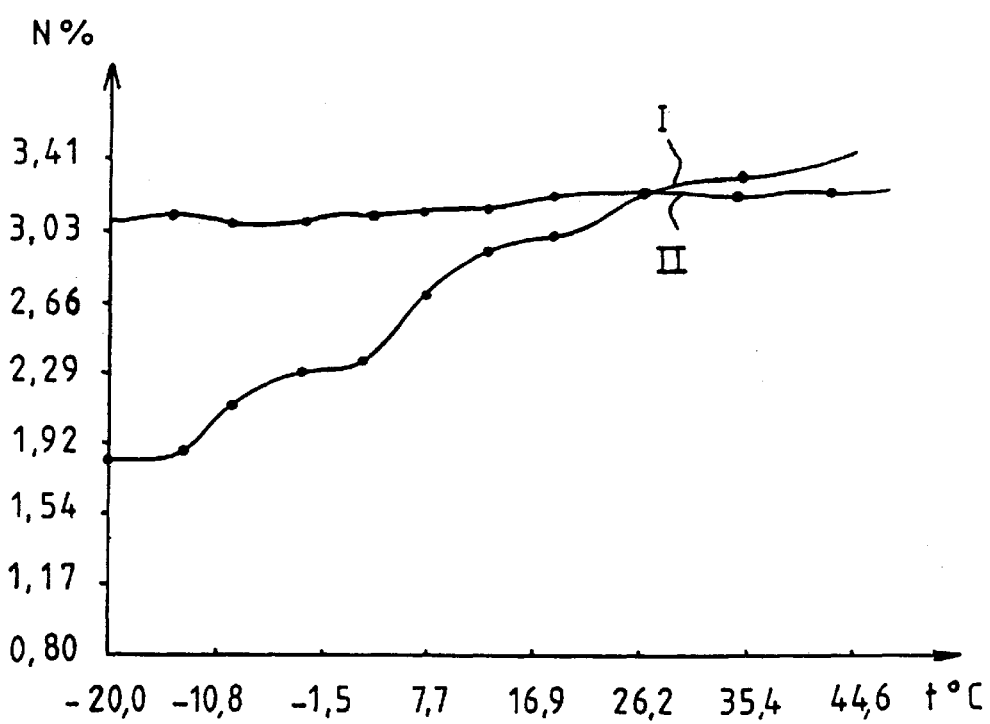
FIG. 4 shows the curves illustrating, as a function of temperature, the information delivered by the analyser in FIG. 1 without temperature compensation and with temperature compensation, respectively.

In fact, FIG. 4 shows that the result provided by means of the method according to the invention for a gas mixture consisting of nitrogen and 3.04% methane is substantially constant, whatever the value of the ambient temperature (curve 1).

On the other hand, the value of the concentration N directly obtained from the law of variation of the transmission coefficient as a function of the concentration at the reference temperature coincides with the actual value only for a temperature corresponding to the reference temperature (26.2° C.) at which the concentration dependence of the transmission coefficient was recorded.

For the extreme values of the operating temperature range of the apparatus, the measured concentration values are completely different from the actual value and the results provided are completely erroneous.

It will be understood that the invention makes it possible to compensate for the variations in density of the gas mixture which are due to variations in the ambient temperature, and also variations in the characteristics of the components making up the device, particularly the optical filters and the semiconductor components, insofar as the standardized value of the transmission coefficient is calculated using the value of the electrical signal $U(0,t)$ formed for a zero gas concentration and for various temperature values.

What is claimed is:

1. Method of determining the concentration of a gas to be analyzed in a gas mixture, by measuring at least one value of the intensity of at least one radiation transmitted through the gas mixture, the method comprising the steps consisting in:

calculating, from at least one measured value of the intensity of at least one radiation transmitted at ambient temperature, the value of a characteristic of the gas mixture having predetermined laws of variation as a function of temperature and as a function of the concentration of gas to be analyzed;

determining the value of said characteristic at a predefined reference temperature different from the ambient temperature from the law of variation of the characteristic as a function of temperature; and determining the value of the concentration of the gas from the law of variation of said characteristic as a function of the concentration.

2. The method according to claim 1, wherein the law of variation of said characteristic as a function of the concentration is determined during a prior calibration step by determining a set of values of the characteristic for various gas concentrations and at the reference temperature.

3. The method according to claim 2, wherein the characteristic consists of the transmission coefficient T(N,t) of the gas mixture, defined by the equation:

$$T(N, t) = \frac{U(N, t)}{U(0, t)} \quad (1)$$

in which:
  T(N,t) denotes the transmission coefficient at the temperature t of the gas mixture containing a concentration N of the gas to be analyzed; and
  U(N,t) and U(0,t) denote the intensity of an electrical signal formed from the output of means for detecting the radiation transmitted through the gas mixture, at the temperature t, the gas mixture containing a concentration N and a zero concentration of the gas to be analyzed, respectively, and the intensity of the electrical signal U(0,t) formed from a mixture containing a zero concentration of gas to be analyzed being obtained during the prior calibration step.

4. The method according to claim 3, wherein during the prior calibration step, the intensity of the electrical signal is measured at the reference temperature for various values of the concentration of the gas to be analyzed and in the absence of the gas to be analyzed in the mixture; and for each concentration value, the transmission coefficient is calculated.

5. The method according to claims wherein the value of the transmission coefficient at the reference temperature is determined during the analysis of the gas mixture from the following equation:

$$T(N, t_{ref}) = T(N, t_a)^{\frac{\ln T(N_0, t_{ref})}{\ln T(N_0, t_a)}} \quad (2)$$

or from the equation:

$$T(N, t_{ref}) = 1 - (1 - T(N, t_a)) \frac{1 - T(N_0, t_{ref})}{1 - T(N_0, t_a)} \quad (3)$$

in which:
  $T(N,t_{ref})$ and $T(N,t_a)$ denote the transmission coefficient of the gas mixture for a concentration N of the gas to be analyzed at the reference temperature and at the ambient temperature, respectively; and
  $T(N_0, t_{ref})$ and $T(N_0, t_a)$ denote the value of the transmission coefficient of the gas mixture for a predetermined concentration $N_0$ of the gas to be analyzed at the reference temperature and at the ambient temperature, respectively.

6. The method according to claim 3, wherein the value of the transmission coefficient at the reference temperature is determined during the analysis of the gas mixture from the following equation:

$$T(N, t_{ref}) = T(N, t_a)^{\frac{\ln T(N_0, t_{ref})}{\ln T(N_0, t_a)}} \quad (2)$$

or from the equation:

$$T(N, t_{ref}) = 1 - (1 - T(N, t_a)) \frac{1 - T(N_0, t_{ref})}{1 - T(N_0, t_a)} \quad (3)$$

in which:
  $T(N,t_{ref})$ and $T(N,t_a)$ denote the transmission coefficient of the gas mixture for a concentration N of the gas to be analyzed at the reference temperature and at the ambient temperature, respectively; and
  $T(N_0, t_{ref})$ and $T(N_0, t_a)$ denote the value of the transmission coefficient of the gas mixture for a predetermined concentration $N_0$ of the gas to be analyzed at the reference temperature and at the ambient temperature, respectively.

7. The method according to claim 6, wherein during the prior calibration step, the intensity of the electrical signal is measured for the gas concentration $N_0$ and for various temperature values encompassing the reference temperature value and the ambient temperature; and for each temperature value, the transmission coefficient is calculated.

8. Analyzer for determining the concentration of gas in a gas mixture contained in an optical analysis cell, comprising:
  first means for emitting a radiation through the optical cell;
  second means for detecting the radiation transmitted;
  both said first means and second means being connected to means for calculating the concentration of said gas;
  said means for calculating the concentration of the gas comprising means for calculating the transmission coefficient ($T(N,t_a)$) of the gas mixture, at ambient temperature ($t_a$); means for calculating the corresponding value of the transmission coefficient ($T(N,t_{ref})$) at a reference temperature different from the ambient temperature ($t_a$); and means for calculating the concentration of said gas by comparing the calculated value of the transmission coefficient at the reference temperature with a set of predetermined values stored in a memory, each value corresponding to a concentration value of said gas.

* * * * *